United States Patent
Carter

(10) Patent No.: US 9,133,087 B2
(45) Date of Patent: Sep. 15, 2015

(54) DIRECT CATALYTIC CONVERSION OF CELLULOSIC MATERIALS TO ETHANOL

(71) Applicant: M K Carter, Lincoln, CA (US)

(72) Inventor: M K Carter, Lincoln, CA (US)

(*) Notice: Subject to any disclaimer, the term of this patent is extended or adjusted under 35 U.S.C. 154(b) by 39 days.

(21) Appl. No.: 14/143,947

(22) Filed: Dec. 30, 2013

(65) Prior Publication Data

US 2015/0183700 A1    Jul. 2, 2015

(51) Int. Cl.
*C07C 31/08* (2006.01)
*C07C 29/00* (2006.01)

(52) U.S. Cl.
CPC ............... *C07C 31/08* (2013.01); *C07C 29/00* (2013.01)

(58) Field of Classification Search
CPC .................................. C07C 29/00; C07C 29/10
See application file for complete search history.

(56) References Cited

U.S. PATENT DOCUMENTS

| | | | | |
|---|---|---|---|---|
| 6,423,145 B1* | 7/2002 | Nguyen et al. | ................... | 127/37 |
| 6,660,506 B2* | 12/2003 | Nguyen et al. | ................ | 435/165 |
| 6,747,067 B2* | 6/2004 | Melnichuk et al. | ........... | 518/702 |
| 7,198,925 B2* | 4/2007 | Foody | ........................... | 435/105 |
| 7,816,568 B2* | 10/2010 | Carter | ........................... | 568/877 |
| 8,455,705 B2* | 6/2013 | Cortright et al. | .............. | 585/240 |
| 8,574,368 B2* | 11/2013 | Holbrey et al. | ................. | 127/37 |

* cited by examiner

*Primary Examiner* — Brian J Davis

(57) ABSTRACT

Catalytic chemical (not biological) reactions conducted during acid digestion of most cellulosic materials, comprising newspaper, wood sawdust, corn cobs, switchgrass and bagasse, are taught for direct conversion to ethanol with conversion efficiencies of at least 90 percent in less than 5 minutes. The cellulose material is thoroughly wet in a salt saturated sulfuric acid medium in the presence of transition metal salt catalysts possessing a degree of symmetry to form ethanol that can be removed by distillation affording a continuous process.

3 Claims, No Drawings

DIRECT CATALYTIC CONVERSION OF CELLULOSIC MATERIALS TO ETHANOL

REFERENCES CITED

U.S. Patent Documents

| | Issue Date | Author | Comments |
|---|---|---|---|
| 8,574,368 | Nov. 5, 2013 | J Holbrey, M Fanselow, KR Seddon, L Vanoye, A Zheng | Preparation of water-soluble cellulose hydrolysis products in an ionic liquid below 150° C., the cations containing a nitrogen or phosphorus atom |
| 8,455,705 | Jun. 4, 2013 | RD Cortwright, PG Blommel | Catalytically reacting $C_4+$ water soluble oxygenated biomass-derived hydrocarbon in an aqueous liquid or vapor phase with $H_2$ using supported (insoluble) catalyst of Re, Cu, Fe, Ru, Pt, Pd, Ni, W, Mo, Ag, Sn at 100° C. to 400° C. and pressure of 72 psig to 1300 psig |
| 7,816,568 | Oct. 19, 2010 | MK Carter | Catalytic conversion of cellulose to ethanol in an acid medium at greater than 200° C. |
| 7,198,925 | Apr. 3, 2007 | B. Foody | Steam and acid hydrolysis of ligno-cellulosics to xylose |
| 6,747,067 | Jun. 8, 2004 | LJ Melnichuk, K Venita | Gasification of cellulose to carbon monoxide and hydrogen for formation of methanol and other products |
| 6,660,506 | Dec. 9, 2003 | QA Nguyen, FA Keller, MP Tucker | Dilute acid hydrolysis with metal salts converting cellulose to sugars |

BACKGROUND

1. Field of Invention

This invention relates to acid digestion and simultaneous catalytic chemical conversion of cellulose materials to ethanol at greater than 90 percent yields, in less than 5 minutes, in a single process step. Specifically cellulosic materials, comprising newspaper, wood sawdust, corn cobs, switchgrass and bagasse, are catalytically converted to ethanol using a soluble catalyst in a sulfuric acid medium in the absence of nitrogen and phosphorous compounds, in air at 110° C. to 180° C. employing catalysts based on transition metal complexes possessing a degree of symmetry as described herein.

2. Description of Prior Art

The chemical process industry has grown to maturity based on petroleum feed stocks, a non-renewable resource, that may become unavailable in the next 80 years. This planet Earth fosters continual growth of abundant carbohydrate based plants including fruits, vegetables, starches, grain food sources, grasses, cotton, shrubs, trees and related natural cellulosic materials. Grains, corn cobs, bagasse, support plant stalks and grasses are, in part, subject to bio-fermentation processes producing ethanol and related products at modest yields. These processes are slow and may convert some ten percent of the cellulose and related materials to ethanol.

Direct Catalytic Conversion of Cellulosic Materials to Ethanol, the subject of this application, teaches conversion efficiencies of at least 90 percent in less than 5 minutes. This process affords complete use of renewable plant materials, the edible portion for human consumption as food and the residual cellulosic materials for conversion to fuels and industrial chemicals leaving no waste.

A number of process paths have previously been taught for chemical conversion of cellulose and hemi-cellulose materials to ethanol. These processes include fermentation of grain and corn, and dilute acid pre-treatment or acidic steam treatment of dried plant materials followed by fermentation of the resulting sugars. They also include enzymatic digestion of cellulose to hemicelluloses and sugars for fermentation as well as gasification of wood chips to carbon monoxide and hydrogen (synthesis gas) to produce products by Fischer-Tropsch type processes. Gasification is expensive and requires some 300° C. to 600° C. in an inert gas environment. Acidic steam treatment subjects bio-mass to pressure with temperatures up to 180° C. Acid digestion or hydrolysis can be conducted at temperatures of 20° C. to 120° C. while fermentation may be operated in the 20° C. to 55° C. range but is usually limited to conversion rates of less than 20 percent.

Ethanol has been made from ethylene gas dissolved in sulfuric acid then diluted and isolated by distillation. It has also been produced by heating ethylene with steam at 300° C. and 1000 to 4000 psi pressure using acid or acidic transition metal oxide catalysts.

U.S. Pat. No. 8,574,368, issued Nov. 5, 2013, teaches a process for preparation of water-soluble cellulose hydrolysis products in an ionic liquid below 150° C., the cations containing a nitrogen or phosphorus atom. U.S. Pat. No. 8,455,705, issued Jun. 4, 2013, describes a method for catalytic hydrogenation of $C_4+$ water soluble oxygenated biomass-derived hydrocarbons in an aqueous liquid or vapor phase using supported (insoluble) catalysts of Re, Cu, Fe, Ru, Pt, Pd, Ni, W, Mo, Ag, Sn at 100° C. to 400° C. and pressure of 72 psig to 1300 psig. U.S. Pat. No. 7,816,568, issued Oct. 19, 2010, disclosed a process for catalytic conversion of cellulose to ethanol in an acid medium above 200° C. U.S. Pat. No. 7,198,925, issued Apr. 3, 2007, taught steam pretreatment of bale quantities of cereal straw, corn stover or grass for hydrolysis of hemicellulose to xylose at 160° C. to 280° C. U.S. Pat. No. 6,747,067, issued Jun. 8, 2004, described a method for gasification of cellulose to carbon monoxide and hydrogen for subsequent formation of methanol and decomposition products. U.S. Pat. No. 6,660,506, issued Dec. 9, 2003, disclosed a process for dilute acid hydrolysis with metal salts converting cellulose to sugars.

There are a number of dilute acid digestion or pre-treatment process disclosed for partial conversion of cellulose to sugars for subsequent formation of ethanol by fermentation, a biological process. Reported conversions were not higher than 65 percent efficiency and were further limited by fermentation conversions to ethanol of less than 20 percent. U.S. Pat. No. 6,660,506, issued Dec. 9, 2003, teaches dilute acid hydrolysis of cellulose, with metal salts, for such partial conversion to sugars.

The present application discloses non-biological use of low valent transition metal catalysts dissolved in an acid medium saturated with inorganic salts, as described in this application, for direct production of greater than 90 percent yields of ethanol from cellulose materials in less than 5 minutes at ambient pressure.

SUMMARY OF THE INVENTION

This invention describes chemical methods using selected members of soluble transition metal catalysts in their lower valence states for conversion of cellulosic natural plant materials to ethanol. Digested lignin acid compounds may also be recovered as by products.

It is an object of this invention, therefore, to provide a catalytic process facilitating conversion of cellulosic materials to ethanol in an acid digestion medium. It is another object of this invention to catalytically convert cellulosic materials to ethanol at 110° C. to 180° C. It is still another object of this invention to catalytically convert plant cellulosic materials to ethanol with conversion efficiencies of at least 90 percent in less than 5 minutes. Other objects of this invention will be apparent from the detailed description thereof which follows, and from the claims.

DETAILED DESCRIPTION OF THE INVENTION

A process for catalytic chemical conversion of cellulosic materials, comprising newspaper, wood sawdust, corn cobs, switchgrass and bagasse, to ethanol and acid lignin by products is taught using soluble transition metal catalysts, comprising vanadium, manganese or cobalt sulfate, chloride or acetate compounds. These catalysts form molecular associations such that directly attached atoms possess $C_{4v}$, $D_{4h}$ or $D_{2d}$ point group symmetry. Catalysts have been designed based on a formal, unpublished, theory of catalysis entitled, *Concepts of Catalysis*, by M. K. Carter, a fundamental mathematical physics theory of catalysis with examples of catalyst design and two detailed applications. The two published applications of the theory are *A Molecular Mechanism For Fischer-Tropsch Catalysis*, J. Mol. Cat. A: Chem. 172, 193-206 (2001) and *Catalytic Air Oxidation of Ambient Temperature Hydrocarbons*, J. Mol. Cat. A: Chem. 200, 191-203 (2003). The catalysts have been produced and tested to prove their activity. The theory of catalysis rests upon a requirement that a catalyst possess a single metal atom or a molecular string such that transitions from one molecular electronic configuration to another be barrier free so reactants may proceed freely to products as driven by thermodynamic considerations. Catalysts effective for chemical conversion of cellulose to ethanol are soluble mono-metal, di-metal, tri-metal and/or poly-metal backbone or molecular string type compounds of the transition metals comprising vanadium, manganese and cobalt. The oxidation state of the soluble transition metal salt is low, typically monovalent or divalent. Mixed transition metal compounds have also been found to be effective catalysts for these chemical conversions.

These catalysts act on cellulose, hemi-celluloses, starches and essentially any available natural carbohydrate compounds to generate free radicals in times believed to be the order of or less than that of a normal molecular vibration. This may be viewed as generation of free radical reactants in equilibrium such that the reaction indicated by the equation $(C_6H_{10}O_5)_x + xH_2O \rightarrow 2xCH_3CH_2OH + 2xCO_2$ may proceed. Water provided in the acid solvent reaction sphere causes hydrolysis of the cellulose such that catalytic exposure to monomer, dimer or oligomer transition metal complexes produces ethanol and carbon dioxide. Thus, ethanol is the product of cellulose reactions and lignin by products are released during the process.

Sulfuric acid is effective in hydrolysis of natural cellulose and hemicellulose containing materials to produce monosaccharides, mostly glucose, but it can also participate in formation of numerous, parallel dehydration by products including carbon, hydroxymethylfurfural, levulinic acid and esterification products all of which can decrease ethanol production. Degradation by products may also be formed depending on the reaction conditions. Reaction conditions are required that maximize production of ethanol and carbon dioxide while suppressing or eliminating formation of by products. One way to favor ethanol formation is to fortify dilute sulfuric acid with inorganic salts. Formation of a liquid reaction medium requires careful packing of the liquid space with metal ions of several sizes in order to achieve an optimum sulfate concentration. Thus, sulfuric acid packed with sodium sulfate, potassium sulfate and zinc sulfate aids conversion of glucose to approximately 60 percent ethanol (plus carbon dioxide) from 63 percent glucose in equilibrium as compared to 30 percent conversion without a salt packed reactant medium.

Preliminary investigation of the effect of acid concentration on cellulose available as paper towels revealed that it dissolved in 68 percent sulfuric acid at ambient temperature in a few minutes producing clear solutions while higher concentrations produced dark, possibly oxidized by products. Treatment of a suspension of corn cob fines at ambient temperature as well as temperatures in excess of 100° C. with 68 percent sulfuric acid demonstrated increased viscosity but only minimal dissolution. Infrared and ultraviolet spectra of aqueous mixtures of zinc chloride and methyl β-D-glucopyranoside revealed that the concentration and stability of zinc complexation increased with the concentration of zinc chloride. The effect of zinc chloride concentration on complex formation with methyl β-D-glucopyranoside paralleled the swelling and loss of crystallinity of cellulose, indicating that the swelling mechanism for cellulose in aqueous zinc chloride solutions depended on the formation of a complex with the vicinal hydroxyl groups on C-2 and C-3 of the D-glucopyranoside repeating unit. Experimental observations of the effect of inclusion of the zinc ion in the acid solution produced essentially clear solutions of corn cob fines at 100° C.

In addition, U.S. Pat. No. 7,816,568, issued Oct. 19, 2010, entitled 'Catalytic Production of Ethanol from Glucose', taught that both a zinc salt and a copper (I) salt were required to reverse the glucose solution equilibrium formation of fructose back to glucose. Without this consideration glucose formation was limited and ethanol formation was less than 65 percent but inclusion of a zinc salt and a copper (I) salt facilitated conversion to greater than 90 percent ethanol.

Catalytic conversion of cellulose/hemicellulose to ethanol was accompanied by an equal molar concentration of carbon dioxide gas that drove the products from the reactor. Experimental measurements demonstrated greater than 90 percent conversion of cellulose/hemicellulose to ethanol for corn cobs, switchgrass and bagasse. Finely divided cellulosic materials were dispersed in the liquid acid reaction medium and the temperature rapidly increased into the 110° C. to 180° C. range, preferably into 120° C. to 160° C. range, to produce an ethanol-sulfuric acid complex. Ethanol can be released for isolation by distillation in the presence of nitric acid. Caution: potential explosion hazard of ethanol-nitric acid mixtures requires they be neutralized immediately following vapor isolation.

Anions of the acidic liquid reaction medium were balanced between sulfate and chloride to optimize ethanol production. In the absence of chloride ion less than fifty percent of the cellulose/hemicellulose was converted to ethanol. An excess of chloride salts caused hydrogen chloride vapor to be released prior to production of ethanol. Thus, this and two other chemical balances were required for optimal production of ethanol: (1) zinc and copper (I) ions were required to shift the equilibrium from fructose to glucose, (2) sulfuric acid, chloride ion and zinc ion were required for optimal dissolution and hydrolysis of natural cellulose/hemicellulose materials, and (3) a balance of sulfate and chloride ions was required to optimize conversion to ethanol.

Catalyst Selection Considerations

A Concepts of Catalysis effort formed a basis for selecting molecular catalysts for specified chemical reactions through computational methods by means of the following six process steps. An acceptable chemical conversion mechanism, involving a single or pair of transition metal atoms, was established for the reactants (step 1). A specific transition metal, such as cobalt, was selected as a possible catalytic site as found in an M or M-M string (step 2), bonded with reactant molecules in essentially a $C_{4v}$, $D_{2d}$ or $D_{4h}$ point group symmetry configuration, and having a computed bonding energy to the associated reactants of 0>E>−60 kcal/mol (step 3). The first valence state for which the energy values were two-fold degenerate was 2+ in most cases although 1+ is possible (step 4). Sulfate, chloride or acetate anions may be chosen provided they are chemically compatible with the metal in formation of the catalyst (step 5). An inspection should also be conducted to establish compliance with the rule of 18 (or 32) to stabilize the catalyst; thus, compatible ligands may be added to complete the coordination shell (step 6). This same process may be applied for selection of a catalyst using any of the first, second or third row transition metals, however, only those with acceptable negative bonding energies can produce effective catalysts. The approximate relative bonding energy values may be computed using a semi-empirical algorithm or by other means. Such a computational method indicated that several of the first row transition metal complexes may be anticipated to produce usable catalysts once the outer coordination shell had been completed with ligands. In general, preliminary energy values computed for transition metal carbohydrate complexes are indicated to produce useable catalysts once bonding ligands have been added.

Catalyst structures commonly including a pair of bonded transition metal atoms may require chelating ligands and/or bonding orbital structures different for each metal. Sulfate, chloride and acetate anions can provide for transition metal associations of vanadium, manganese or cobalt ions in solution. The following compounds comprise a limited selection of examples. For the first row transition metals vanadium catalysts comprise vanadyl sulfate and ethylenediamine (EDA) links the metals in $(VCl_2)_2EDA_2$. The compound $[V(THF)_4Cl_2][V(CO)_6]_2$, for which ethanol or other reactants may displace a CO and/or a THF ligand, and the compound $V_2(SO_4)_3$ are also catalytic. Manganese catalysts comprise $(MnCl_2)_2EDA_2$, $K_2[Mn_2Cl_6(H_2O)_4]$ and $Mn_2(C_5H_8O_2)_4(H_2O)_2$. Cobalt catalysts comprise $Co_2(C_6H_5O_2)_2(C_6H_6O_2)_2$, $Co_2(C_5H_8O_2)_4(H_2O)_2$, $Co(C_6H_5O_2)_2(C_6H_5O_2)_2$, $Co_2(C_6H_5O_2)_4$ and $Co_2(SO_4)_2$.

A select number of single transition metal atom catalyst complexes containing four ligands each and exhibiting the required symmetry, belonging to the required point group symmetry may also be catalytic. These catalysts comprise $M(II)(C_6H_5O_2)_2(C_6H_6O_2)_2$, $M(II)(p-C_6H_5O_2)_2$, $M(II)(C_6H_6NO)_2(C_6H_7NO)_2$ and $M(II)(O_2CCH_3)_2(HO_2CCH_3)_2$ plus possible solvation ligands where M represents vanadium, manganese or cobalt. In some complexes the transition metal atom may be monovalent or trivalent. Select second and third row transition metal compounds may also be catalytic.

Description of Chemical Conversion

Cellulosic material conversions were conducted in a dilute sulfuric acid medium saturated with inorganic salts by heating cellulose materials in an open reactor, using a small amount of catalyst, to a temperature in the range of 110° C. to 180° C. The final temperature was maintained for approximately five minutes before the reactor was allowed to cool to room temperature. Chemicals are reagent grade unless otherwise stated.

EXAMPLE 1

Corn Cob to Ethanol

A 40 mL glass vial was fit with a 6 inch long by ¼ inch diameter stainless steel vent line formed with a 4 inch section followed by a bend to 135 degrees and insulated by a rubber vacuum tube providing a 2 inch long effluent end. Added to the glass vial were 0.094 gram of potassium chloride, 1.67 gram of USP grade sodium chloride, 0.53 gram of zinc sulfate heptahydrate, 0.0009 gram of manganese (II) sulfate monohydrate catalyst, 0.0011 gram of copper(I) chloride and 6.43 grams of 98 percent sulfuric acid diluted with 3.06 grams of water. The vial was cooled to RT, chips of dry corn cob were ground to a fine powder, 0.80 gram of corn cob dust was dispersed in the reaction mixture and the vent line was attached. The vial was immersed into a 155° C. propylene glycol bath and heated for 5 minutes. After one to two minutes 7.77 grams of liquid and solid product was discharged from the stainless steel vent to a glass receiver. A 0.197 gram portion of this product (liquid plus solid) was analyzed using a Nitrochromic Acid reagent demonstrating 94 percent conversion of cellulose/hemicellulose to ethanol. This small quantity reaction (catalyst concentration not optimized) yielded a turnover number (TON) of 1,440 mols of ethanol per mol of catalyst. The discharged product also contained quantities of solid lignin acid residue.

EXAMPLE 2

Corn Cob to Ethanol

A 40 mL glass vial was fit with a short u-shaped stainless steel vent line insulated by a rubber vacuum tube. Added to the glass vial were 0.094 gram of potassium chloride, 1.67 gram of USP grade sodium chloride, 0.53 gram of zinc sulfate heptahydrate, 0.005 gram of cobalt (II) oxalate dehydrate catalyst, 0.006 gram of copper(I) chloride (see discussion) and 6.43 grams of 98 percent sulfuric acid diluted with 3.06 grams of water. The vial was cooled to RT, chips of dry corn cob were ground to a fine powder, 0.80 gram of corn cob dust was dispersed in the reaction mixture and the vent line was attached. The vial was immersed into a 155° C. propylene glycol bath and heated for 5 minutes. After one to two minutes 7.58 grams of liquid and solid product was discharged from the stainless steel vent to a glass receiver. A 0.12 gram portion of this product was analyzed using a Nitrochromic Acid reagent demonstrating 98 percent conversion of cellulose/hemicellulose to ethanol. The purged liquids also contained quantities of solid lignin acid residue.

EXAMPLE 3

Corn Cob to Ethanol

A 40 mL glass vial was fit with a short u-shaped stainless steel vent line insulated by a rubber vacuum tube. Added to the glass vial were 0.094 gram of potassium chloride, 1.67 gram of USP grade sodium chloride, 0.53 gram of zinc sulfate heptahydrate, 0.002 gram of vanadyl sulfate catalyst, 0.006 gram of copper(I) chloride (see discussion) and 6.43 grams of 98 percent sulfuric acid diluted with 3.06 grams of water. The vial was cooled to RT, chips of dry corn cob were ground to a fine powder, 0.80 gram of corn cob dust was dispersed in the reaction mixture and the vent line was attached. The vial was immersed into a 154° C. propylene glycol bath and heated for 5 minutes. After one to two minutes 8.44 grams of liquid and solid product was discharged from the stainless steel vent to a glass receiver. A 0.202 gram portion of this product was analyzed using a Nitrochromic Acid reagent demonstrating 97 percent conversion of cellulose/hemicellulose to ethanol. The purged liquids also contained quantities of solid lignin acid residue.

EXAMPLE 4

Corn Husk to Ethanol

A 40 mL glass vial was fit with a short u-shaped stainless steel vent line insulated by a rubber vacuum tube. Added to the glass vial were 0.094 gram of potassium chloride, 1.67 gram of USP grade sodium chloride, 0.53 gram of zinc sulfate heptahydrate, 0.005 gram of manganese (II) sulfate monohydrate catalyst, 0.006 gram of copper(I) chloride (see discussion) and 6.43 grams of 98 percent sulfuric acid diluted with 3.06 grams of water. The vial was cooled to RT, leaves of dry corn husk were ground to a fine powder, 0.80 gram of corn cob dust was dispersed in the reaction mixture and the vent line was attached. The vial was immersed into a 155° C. propylene glycol bath and heated for 5 minutes. After one to two minutes 7.77 grams of liquid and solid product was discharged from the stainless steel vent to a glass receiver. A 0.12 gram portion of this product was analyzed using a Nitrochromic Acid reagent demonstrating 93 percent conversion of cellulose/hemicellulose to ethanol. The purged liquids also contained quantities of solid lignin acid residue.

EXAMPLE 5

Switchgrass to Ethanol

A 40 mL glass vial was fit with a rubber vacuum tube insulating a short u-shaped stainless steel vent line. Added to the glass vial was a mixture of 0.094 gram of potassium chloride, 1.67 gram of USP sodium chloride, 0.33 gram of zinc chloride, 0.006 gram of manganese (II) sulfate monohydrate catalyst, 0.006 gram of copper(I) sulfate (see discussion), 3.06 grams of water and 6.94 grams of sulfuric acid. The vial was cooled to RT, a bunch of dry switchgrass was ground to a fine powder, 0.80 gram of switchgrass dust was dispersed in the reaction mixture and the vent line was attached. The vial was rapidly heated to approximately 155° C. as 6.24 mL of liquid plus solid product was discharged to a glass receiver and a 0.12 gram portion of this product was analyzed using a Nitrochromic Acid reagent demonstrating 91 percent conversion of cellulose/hemicellulose to ethanol plus carbon dioxide minutes after heating was initiated. The purged liquids also contained quantities of solid lignin acid residue.

EXAMPLE 6

Bagasse to Ethanol

A 40 mL glass vial was fit with a short u-shaped stainless steel vent line insulated by a rubber vacuum tube. Added to the glass vial were 0.094 gram of potassium chloride, 1.67 gram of USP grade sodium chloride, 0.53 gram of zinc sulfate heptahydrate, 0.005 gram of manganese (II) sulfate monohydrate catalyst, 0.005 gram of copper(I) chloride (see discussion) and 6.43 grams of 98 percent sulfuric acid diluted with 3.06 grams of water. Strips of sugar cane (bagasse) were boiled in water, rinsed several times to remove residual sugar, dried and ground to a fine powder. The vial was cooled to RT, 0.80 gram of bagasse dust was dispersed in the reaction mixture and the vent line was attached. The vial was immersed into a 155° C. propylene glycol bath and heated for 5 minutes. After one to two minutes 7.39 grams of liquid and solid product was discharged from the stainless steel vent to a glass receiver. A 0.12 gram portion of this product was analyzed using a Nitrochromic Acid reagent demonstrating 96 percent conversion of cellulose/hemicellulose to ethanol. The purged liquids also contained quantities of solid lignin acid residue.

What is claimed:

1. Catalytic chemical conversion of cellulosic materials, comprising newspaper, wood sawdust, corn cobs, switchgrass and bagasse, to ethanol using soluble catalysts in a sulfuric acid medium saturated with inorganic salts in the absence of added nitrogen and phosphorous compounds, in air at 110° C. to 180° C.

2. Catalytic chemical conversion of cellulosic materials, comprising newspaper, wood sawdust, corn cobs, switchgrass and bagasse, to ethanol using soluble catalysts in a sulfuric acid medium saturated with inorganic salts in the absence of added nitrogen and phosphorous compounds, in air at 110° C. to 180° C. with conversion efficiencies of at least 90 percent in less than 5 minutes.

3. Catalytic chemical conversion of cellulosic materials comprising newspaper, wood sawdust, corn cobs, switchgrass and bagasse, to ethanol using soluble catalysts in a sulfuric acid medium saturated with inorganic salts in the absence of added nitrogen and phosphorous compounds, in air wherein catalysts possessing a degree of symmetry are formed from transition metal compounds comprising vanadium, manganese, cobalt salts or combinations thereof, at 110° C. to 180° C. with conversion efficiencies of at least 90 percent in less than 5 minutes.

* * * * *